US008715208B2

(12) United States Patent
Hodgins et al.

(10) Patent No.: US 8,715,208 B2
(45) Date of Patent: May 6, 2014

(54) ASSESSMENT OF GAIT (75) Inventors: Diana Hodgins, Codicote (GB); Andrew Whalley, Codicote (GB)

(73) Assignee: European Technology for Business Limited (GB)

( * ) Notice: Subject to any disclaimer, the term of this patent is extended or adjusted under 35 U.S.C. 154(b) by 188 days.

(21) Appl. No.: 13/128,834

(22) PCT Filed: Nov. 13, 2009

(86) PCT No.: PCT/GB2009/051538
§ 371 (c)(1),
(2), (4) Date: May 11, 2011

(87) PCT Pub. No.: WO2010/055352
PCT Pub. Date: May 20, 2010

(65) Prior Publication Data
US 2011/0218463 A1 Sep. 8, 2011

(30) Foreign Application Priority Data
Nov. 14, 2008 (GB) .................................. 0820874.6

(51) Int. Cl.
*A61B 5/117* (2006.01)
*A61B 5/103* (2006.01)
(52) U.S. Cl.
USPC ........................................................ 600/595

(58) Field of Classification Search
USPC ................... 600/595; 119/421, 712, 859, 174
See application file for complete search history.

(56) References Cited

U.S. PATENT DOCUMENTS

| 2005/0010139 A1* | 1/2005 | Aminian et al. ............... 600/595 |
| 2006/0000420 A1* | 1/2006 | Martin Davies .............. 119/174 |
| 2007/0130893 A1 | 6/2007 | Davies |

FOREIGN PATENT DOCUMENTS

| WO | 2003/065891 | 8/2003 |
| WO | 2004/078255 | 9/2004 |
| WO | 2006/009959 | 1/2006 |

OTHER PUBLICATIONS

International Search Report/Written Opinion; PCT/GB2009/051538; mail date: Mar. 30, 2010.

* cited by examiner

*Primary Examiner* — Brian Szmal
(74) *Attorney, Agent, or Firm* — Andrus Intellectual Property Law (57) ABSTRACT

A method of monitoring or assessing the motion of the limbs of a body when performing repetitive cyclic activity uses inertial measurement units secured to each of the limbs to be monitored. The operation of all of the IMUs is synchronized by way of a pulse from a computer. On performing the repetitive cyclic activity such as walking, running, trotting or galloping, the outputs of the IMUs are assembled and analyzed in realtime, to determine the relative phase of the limb movements, from which an assessment of the gait may be made.

18 Claims, 14 Drawing Sheets

ASSESSMENT OF GAIT

The present application is the U.S. national stage application of International Application PCT/GB2009/051538, filed Nov. 13, 2009, which international application was published on May 20, 2010 as International Publication WO 2010/055352. The International Application claims priority of British Patent Application 08 20874.6, filed Nov. 14, 2008.

This invention relates to a method of monitoring or assessing the motion of the limbs of a human or animal body, when performing repetitive cyclic activity, such as (in the case of a human) walking, running, rowing or swimming and (in the case of a horse) walking, trotting, cantering and galloping.

Though this invention is applicable to the repetitive cyclic activities of both humans and a variety of different animals (but mainly mammals) the invention is of particular interest with horses and humans and so will be described primarily with reference to those, in the following. It is however to be understood that the invention is not to be regarded as limited to its use with horses or humans.

There are many reasons why there is an interest in understanding the movement of the limbs of horses and humans. In the case of horses, there are specific interests in whether a horse is exhibiting lameness as well as expanding the knowledge base of performance horses, describing aspects such as how different breeds move, horse/rider interaction and the effect of surfaces and climatic conditions on the performance of a horse. The modern horse is predominantly used for athletic purposes and has to perform on a variety of surfaces and terrains. There is increasing recognition that these are important factors in the performance ability and soundness of a horse and can have an effect on the gait pattern of an individual horse.

Lameness is one of the main causes of a horse not reaching its full athletic potential and has massive financial implications to owners and trainers worldwide. Therefore early recognition of an alteration of normal gait, due to a functional or structural disorder in the locomotor system affected by lameness, is vital for the welfare of the horse. Observation of the gait patterns of lameness usually relies on comparison with a normal reference, commonly from the horse itself, either assessing symmetry or asymmetry of locomotion or comparing the horse before and after diagnostic nerve and joint blocks with local analgesia. Accurate assessment by eye requires experience and has been documented to have variability between assessors.

Kinetic and kinematic studies have been used to understand horse limb locomotion for different lameness conditions but have revealed few consistencies. One study describes adaptations in trot to forelimb lameness by a reduced suspension phase following the affected diagonal pair's stance phase compared to the non-affected pair and a higher flight arch than normal in the unaffected ipsilateral forelimb. Adaptive changes to hind limb lameness do not affect the suspension phase in trot but do result in a shorter lower flight arch from the affected limb compared to the non-affected ipsilateral limb. Co-ordination of the limb placement may be affected by asymmetric suspension during the step from lame to sound forelimb or a reduced loading in stance, possibly resulting in a difference in the cyclic timing of the limbs.

Measurable performance indicators are useful for selecting a young horse with potential, or for the expected performance of horses in training. The basis of dressage training is to develop symmetry, rhythm and regularity in all gaits. There is little at present known about how horses respond stride by stride in their gait patterns and limb cycle timing to pain, training techniques, changing terrain and surfaces. Current techniques employed to analyse the gait of a horse include: accurate assessment visually by experienced clinicians; optical cameras and force plates in a 'gait laboratory'. With the advancement of inertial based systems using accelerometers and gyroscopes, over the last decade such systems have also been reliably used in biomechanics research applications to describe various aspects of inter-stride variability, stride duration and swing and stance phase.

Accelerometers have been used to assess a horse's stride length, frequency and aspects of stride timing variables as well as asymmetries in gait pattern, resulting from lameness. Accelerometers attached to the hoof wall of a single limb have been proven sensitive enough to detect foot on and foot off with respect to a surface, and variability in hoof surface interaction on different surfaces at speed. The alignment and fixing of the accelerometer is critical and typically has been glued to the hoof wall in order to maintain alignment and contact throughout a trial. Further, the accelerometer may be protected from abrasion using electrical insulation tape. The associated electronics for the accelerometer have been mounted on the cannon under an exercise bandage.

The progress in microsystem technology and microelectronics has been significant and has resulted in sensor modules small and light enough to be mounted to a horse's limb providing a reliable method of evaluation of gait characteristics of numerous continuous strides derived from cyclical movements in field situations. These second generation inertial sensors incorporate gyroscopes with accelerometers and have the advantage of being able to collect rotational and linear data. Thus in principle the trajectory of the mounting point of the sensor can also be tracked over time. Although these sensors are still relatively new, studies combining accelerometers and gyroscopes have proved reliable in detecting fore and hind limb lameness. The sensors have also been used to measure the phase difference between the left and right tuber coxae asymmetric movement in lame horses. Time elapsing between each hoof midstance has been described in galloping thoroughbred racehorses using the dosoventral acceleration trace from an accelerometer attached to the sternum. The same sternum attached accelerometer sensor has also been used to collect data from trotting standard-bred horses of hoof-landing, midstance and propulsion.

There have been proposals to use four hoof-mounted Inertial Measurement Units (IMUs) to study the effect of speed on the stride parameter in race horses, to define stance onset, end, duration and aerial phase. However it is not easy to attach IMUs on to hoof walls sufficiently stably without glue, so making it impractical for everyday use outside a research situation.

For the human, the assessment of gait relates directly to his/her ability to walk or run in a symmetric, uniform manner. This is relevant to people with a problem with one or both of their lower limbs or their back, which can cause asymmetry in movement, or their nervous system which can affect their lower limb movement.

For people with a knee injury, their walking pattern is not symmetric. It is important before surgery that the pre-treatment situation is known and documented. Currently this is assessed visually by experienced physiotherapists or orthopaedic clinicians, or in special cases using optical cameras and force plates in a 'gait laboratory'.

People with a back problem tend to walk with an asymmetric gait in order to relieve the pain. This puts additional strain on particular joints and muscles, which may ultimately lead to surgery.

Some people change their gait as they get older, making them less stable when walking. If this change in gait goes undetected then the person may fall, causing distress and often requiring surgical intervention. If the abnormal gait pattern was detected before a fall occurred then exercises could be introduced and ideally prevent falls.

These are just some of the examples where a person's health relates to his/her gait profile. There are many others, including diabetic patients prone to leg ulcers, hydrocephalus patients, people with Parkinson's disease and people fitted with a prosthesis or orthosis.

There are also applications where professional sports people could benefit from an improvement in their gait profile. However, in order to identify where improvements may be made, it is necessary first to quantify the gait. Conventionally, this is done using optical systems and/or force plates in a controlled environment. Recently the progress in microsystem technology has enable stride length and stride frequency to be determined when sensors are mounted on the foot, although the accuracy is not sufficiently good to identify subtle changes in gait which introduce asymmetries in movement.

The measurement techniques developed to date, to determine the swing and stance phase on each limb and their relative phasing, rely on event monitoring and specifically foot down and foot off. The limitations of this approach when using an optical system are the limited amount of data and the required processing time. When using an inertial based system the limitation is that the sensor module must be mounted on a hoof or foot. Hence, both of these approaches are unsuitable for everyday use.

It is a principal aim of this invention to provide a new method for characterising the temporal relationship between the motions of the limbs of a human or animal performing repetitive cyclic activity. In the case of a horse, the method allows the monitoring of the motions of each cannon, in a variety of gaits. In the case of a human it is the thigh and calf movement on each leg which may be monitored. In its preferred aspects, this method is based on the assumption that the movements in a horse of the metacarpal/tarsal region can be represented by waveforms of similar shape and identical frequency. For the human it is the movement of the thigh/calf region. The cross-correlation function is then used to determine the phase angle between a designated reference and the other three regions.

According to the broadest aspect of this invention, there is provided a method of monitoring or assessing the motion of the limbs of a human or animal body when performing repetitive cyclic activity, comprising the steps of:
  securing a respective sensor measurement unit to each of the limbs to be monitored, each sensor measurement unit being associated with a receiver for data generated thereby;
  synchronising the operation of the sensor measurement units;
  assembling and analysing the data from the sensor measurement units to determine the relative phase of the limb movements in the course of the performance of the repetitive cyclic activity.

The method of this invention is based on the hypothesis that limb mounted sensor measurement units can be used to measure the temporal phase relationships between limb cycles. For horses this is at different gaits on surfaces of different physical characteristics. For humans it is at different speeds on a variety of terrain, including stairs. Preferably, each such sensor measurement unit is in the form of an inertial measurement unit, including three mutually orthogonal gyroscopes and accelerometers and advantageously each comprises a microelectromechanical systems (MEMS) device, though it is possible to implement the method with an inertial measurement unit in the form of a single z-axis gyro.

A particular aim of this invention has been to develop a robust method of measuring the temporal limb phase relationships between limb cycles. In the case of a horse, this can be when in different gaits and on surfaces of different physical characteristics. In the case of a human, it can be at different speeds and terrains including stairs. As a consequence, it has been possible to perform pilot investigations on the effect of gait, surface and direction on the phase difference characteristics of the locomotion of horses and humans.

In a preferred method, the assembled data is indicative of at least one of limb rotation and joint rotation. In the case of a horse, the sensor measurement units may be secured to determine either fetlock joint rotation or fore knee joints (on the fore legs) and hind hock joints (on the hind legs). Instead of determining joint rotation, or perhaps in addition to that, the assembled data may be indicative of at least limb spatial position as the limb moves in the course of the cyclic activity. In the case of a human, the sensor measurement units may be on either the calf and/or thigh or foot on each leg and could also measure knee or ankle flexure angle.

The data from each sensor measurement unit may be stored locally in the receiver mounted on the human or animal body at a convenient location, for subsequent uploading to a computer wherein the data is analysed for an assessment of the phasing of the limbs during the cyclic activity. In the alternative, the data from each sensor measurement unit may be transmitted in real time to a data receptor remote from the human or animal body, from where the data is loaded into a computer for analysing for an assessment of the phasing of the limb movements. The assessment may comprise mere monitoring of the gait, or could comprise observing, calculating or recording the gait, as required for the particular intended purpose.

By way of example various preferred aspects of the method of this invention as applied to a horse and the apparatus used in performing those methods will now be described in detail. Reference will be made in the following to the accompanying drawings, in which.

Figures 1A, 1B:
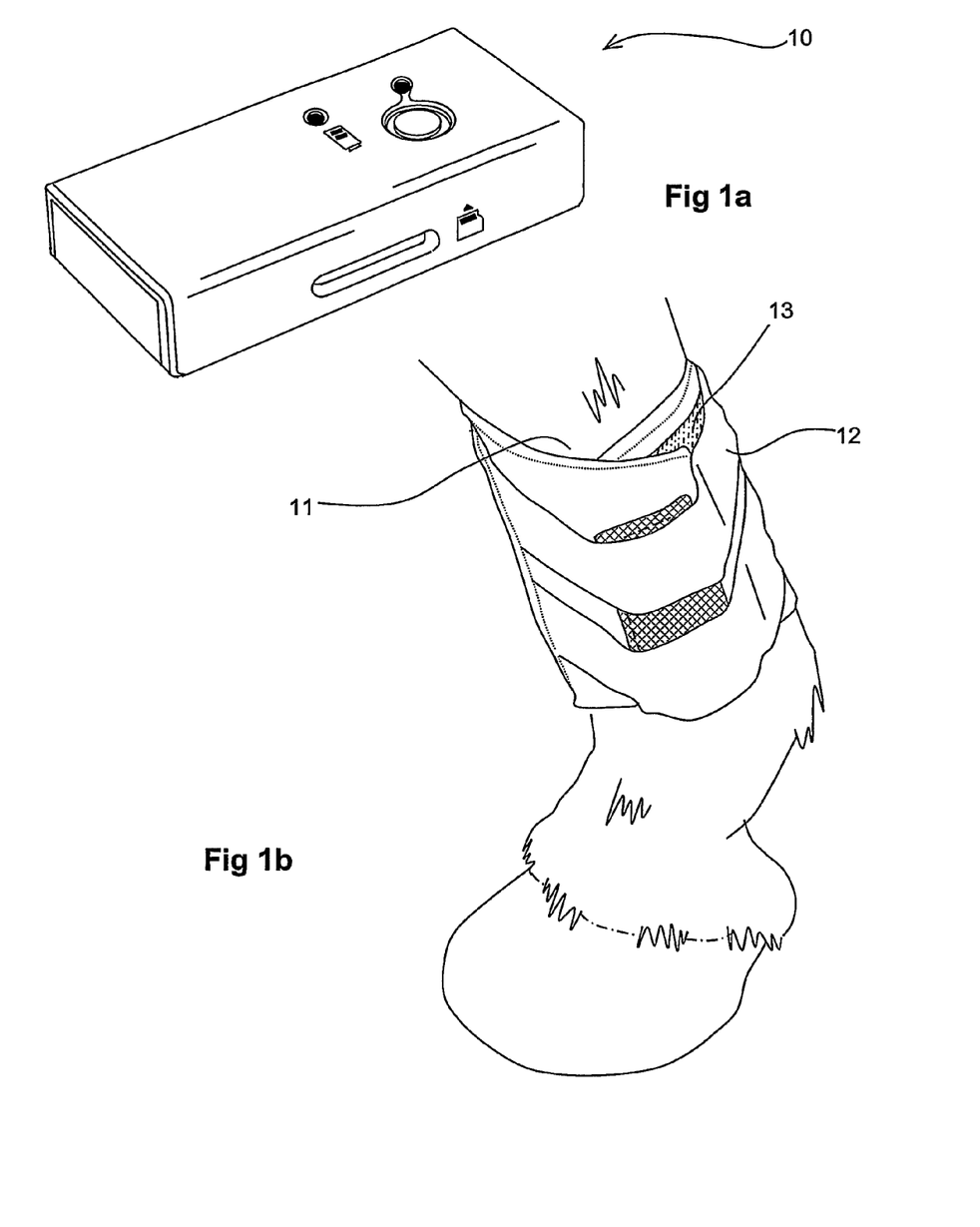
FIGS. 1*a* and 1*b* respectively show the sensor unit and the sensor located in a brushing boot.

Trials were carried out using commercially available inertial measurement units (IMUs) that record on six-degrees-of-freedom (6DOF), in this case the Pegasus 1 Unit: ETB, Codicote United Kingdom. Each IMU is shown at 10 in FIG. 1a and had a total weight of 54 grams, measuring 73×36×19 mm. Each IMU contained a tri-axial 5g accelerometer and three single axis, 1200 deg/s gyroscopes followed by anti-aliasing filters with a cut-off frequency of approximately 50 Hz, the outputs of which were sampled with a 12 bit analogue-to-digital converter at a frequency of 102.4 Hz.

Figure 12:
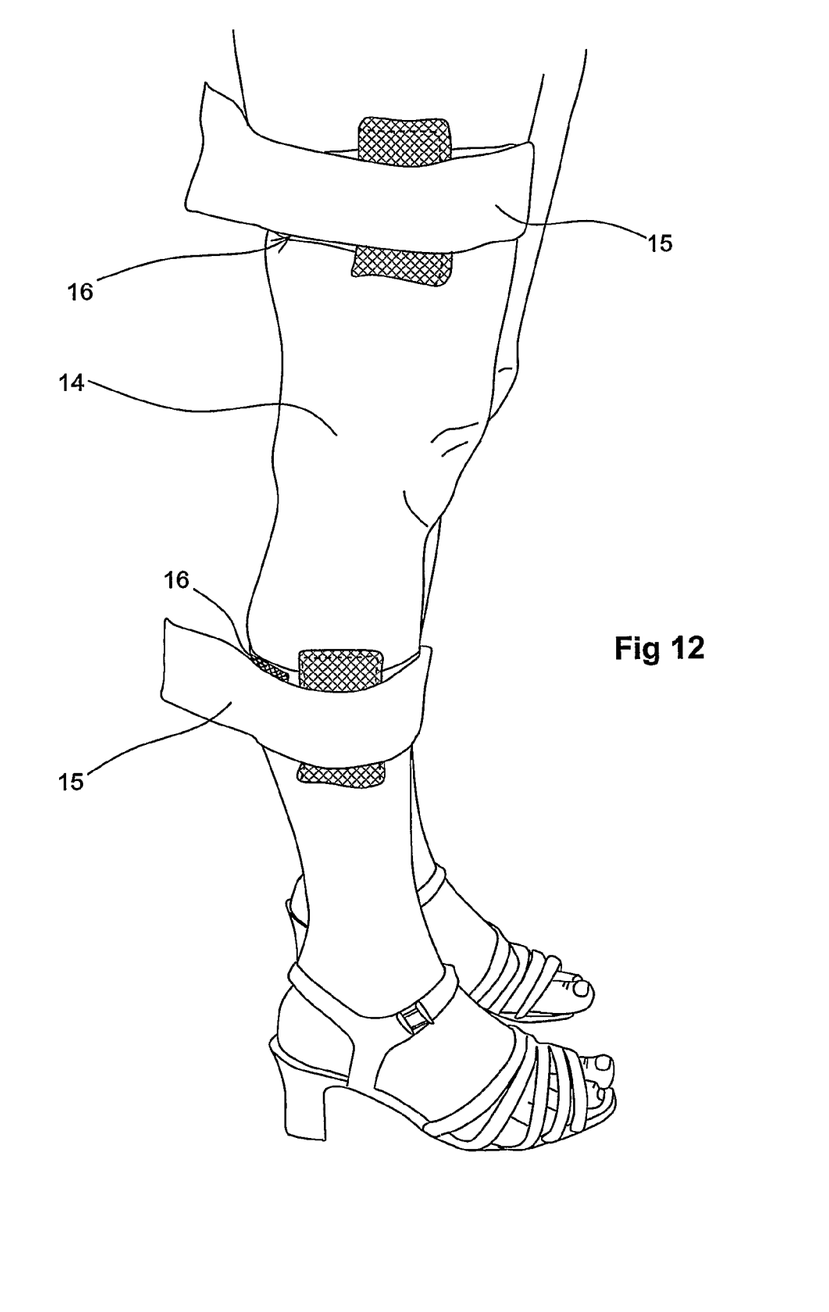
FIG. 12 shows two sensor units mounted on the calf and thigh of a human leg, using custom made straps.
Figure 13:
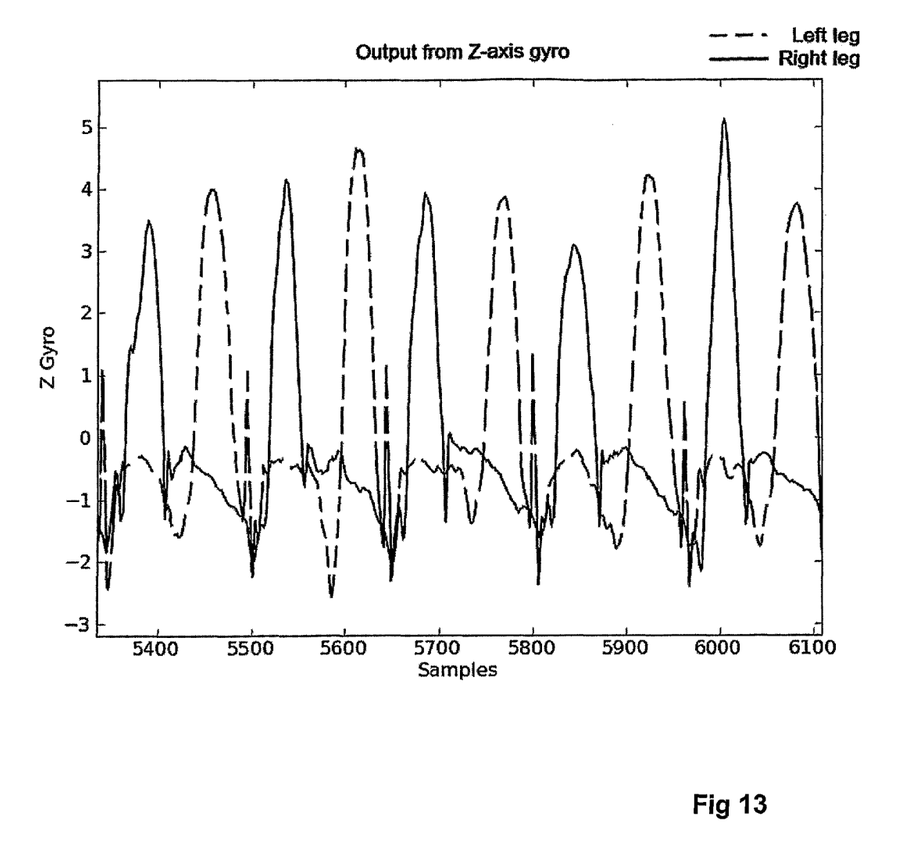
FIG. 13 shows the processed output for a person walking.
Figure 14:
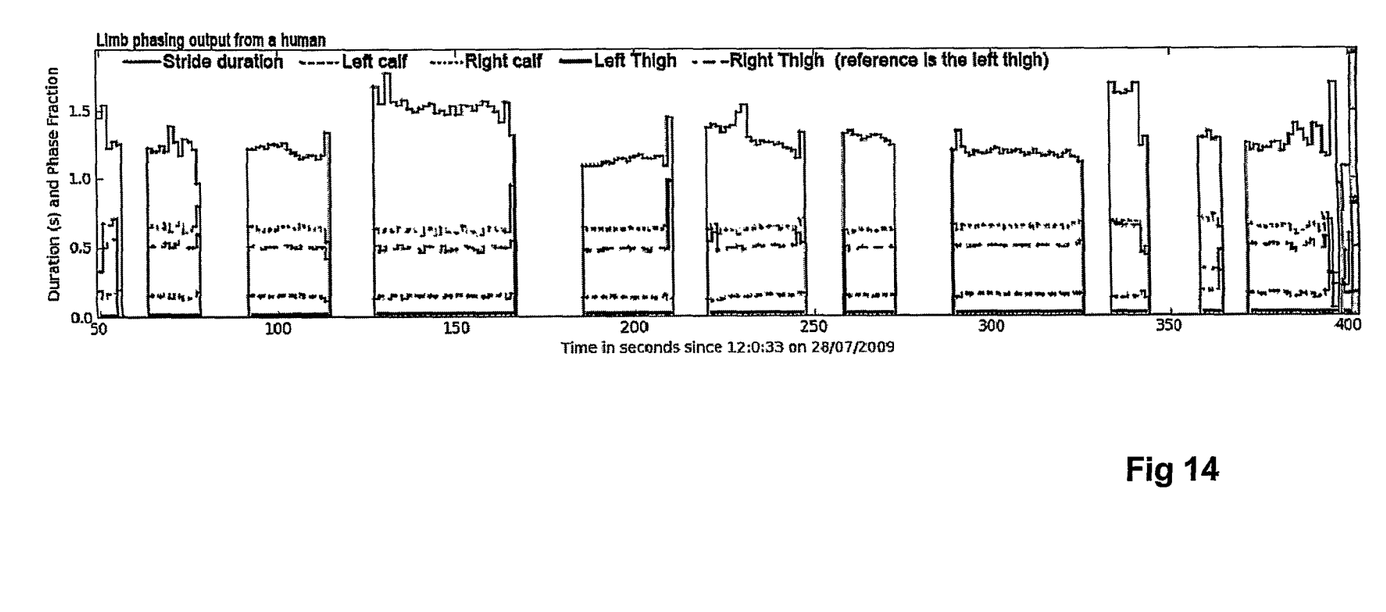
FIG. 14 shows the limb phasing output from a human.

Each IMU was attached to a limb 11 of a horse (FIG. 1b) by means of a fabric strap 12 provided with hook-and-loop fasteners 13, so that each sensor recorded acceleration and angular velocity in a frame of reference that is attached to, and moves with, the limb of the horse. FIG. 12 shows a similar IMU attached to a human leg 14 again by means of a strap 15 provided with hook-and-loop fasteners 16, to allow the recording of the acceleration and angular velocity of the limb to which the IMU is attached. Each IMU was factory-set to within 1 ppm (equivalent to 3.6 milliseconds per hour) of a reference traceable to national standards with the aim of achieving less than 10 milliseconds per hour relative drift between the units after synchronisation. The sample interval is 1/102.4 or 9.77 mS which is greater than the relative drift between two units in one hour. At the beginning of each day of data acquisition, the IMUs were synchronised with a computer clock by a simultaneous pulse sent to each unit, and were calibrated for recording using specifically written software—Poseidon version 4.0 (ETB, Codicote, UK).

Data Processing

A complex set of signals comprising acceleration and rotation data along the three orthogonal axes of the local coordinate system of the unit was sampled at 102.4 Hz.

Figure 2:
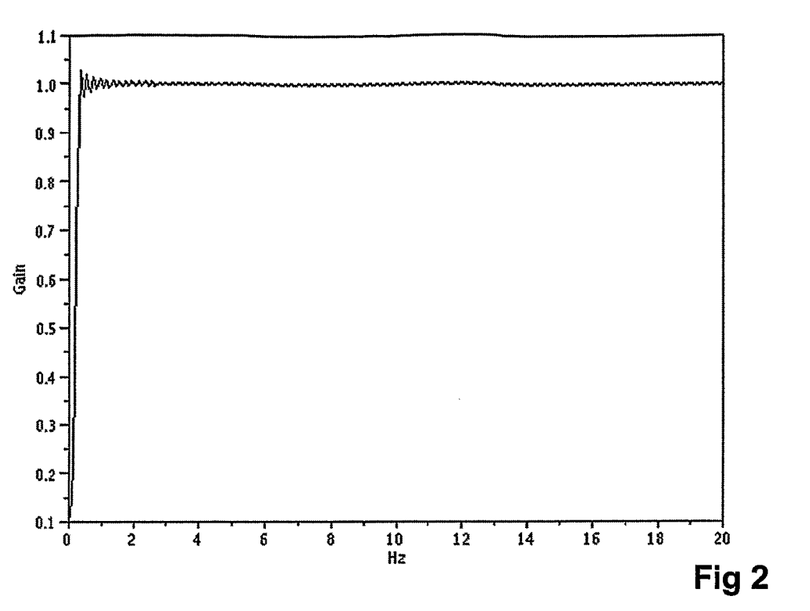
FIG. 2 shows the high pass filter frequency response of gain with frequency.

The outputs of the analogue-to-digital converter were transformed into ISO units using a calibration table appropriate for each device. The transformed data was filtered using a finite impulse response high pass digital filter with a cut-off frequency of 0.15 Hz and unity pass band gain. This frequency response is shown in FIG. 2.

Figure 3:
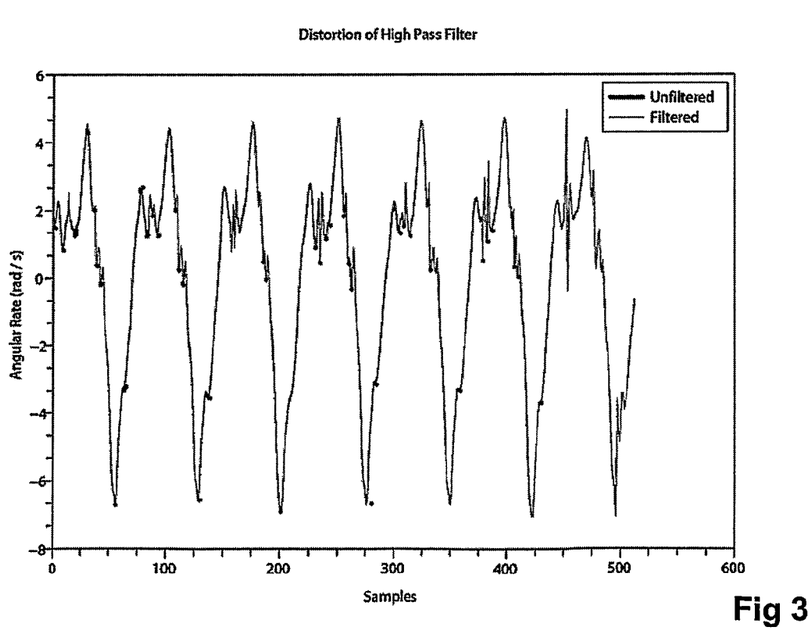
FIG. 3 shows the output signal from a gyro trial, with the pre and post output signal showing the minimal effect of filtering using a high pass filter system.

The flat pass band response and the extremely low cut-off frequency of the filter impose minimal distortion on the measured signal (see FIG. 3). This filtering process serves merely to remove any potential residual offset caused by temperature and/or time sensor drift and has no effect on the sensor output due to the horse movement.

A statistical correlation approach was used to determine the temporal relationships between the respective limbs, and to evaluate the relative performance of both the accelerometers and gyroscopes in measuring these temporal relationships. This was based on an assumption that each limb displayed a similar cyclic or sinusoidal motion. The cross correlation served two purposes: firstly the magnitude of its coefficient gave an indication of the validity of the underlying assumption of the similarity in the cyclic limb motion between limbs; and secondly, a temporal shift between the limb cycles was calculated where the coefficient was maximal.

Given two similarly shaped periodic signals of the same frequency it was then possible to use the cross-correlation function to determine the phase relationship between those signals. The cross-correlation is a function of a time delay, and is defined as:

$$(f*g)(t) \equiv \int_{-\infty}^{+\infty} f^*(\tau)g(t+\tau)d\tau$$

where f* denotes the complex conjugate of f.

The discrete cross-correlation function equivalent is defined as:

$$(f*g)[n] \equiv \sum_{m=-\infty}^{+\infty} f^*[m]g[n+m]$$

This monotonically increasing time delay is added to one of the functions, effectively shifting it in time with respect to the other. For each value of time delay the product of the shifted and un-shifted functions is integrated. The more similar the un-shifted and shifted functions become, the higher will be the accumulated value. This is because wherever a shifted and un-shifted function has the same sign their product will be positive. Conversely, wherever a shifted and un-shifted function has opposite signs their product will be negative and this will tend to decrease the overall integrity. Therefore the time shift corresponding to the peak of the cross-correlation function represents the point of closest match.

Figure 4:
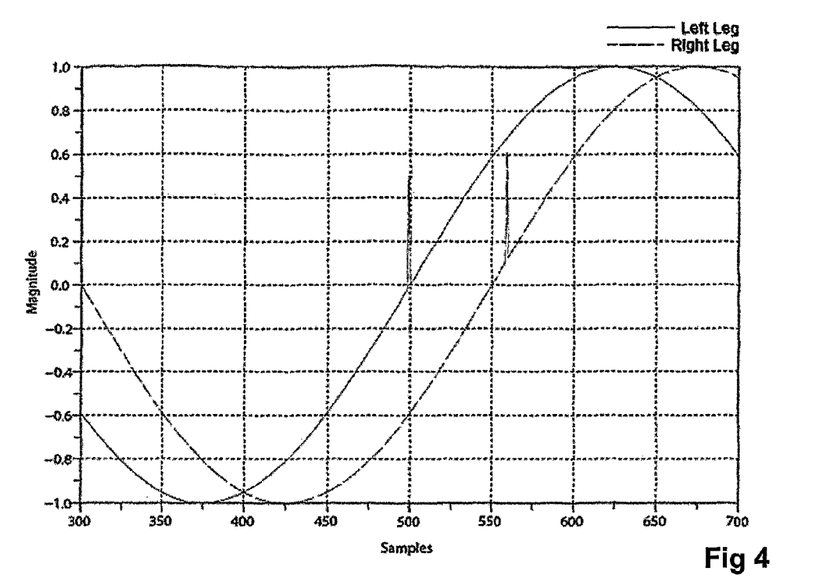
FIG. 4 is a diagrammatic representation of theoretical signals from two limbs of one horse from an inertial measurement unit.

A theoretical example of the cyclic motion of the fore and hind limbs is given in FIG. 4. These cyclic motions can be represented as two sine waves. The small disturbances (minor peaks) have been added as possibly representing the point of hoof contact. Using the cross correlation method the phase between the two signals would be 50 samples, but if the disturbances were aligned it would be 60 samples.

Horse Example

Figure 5:
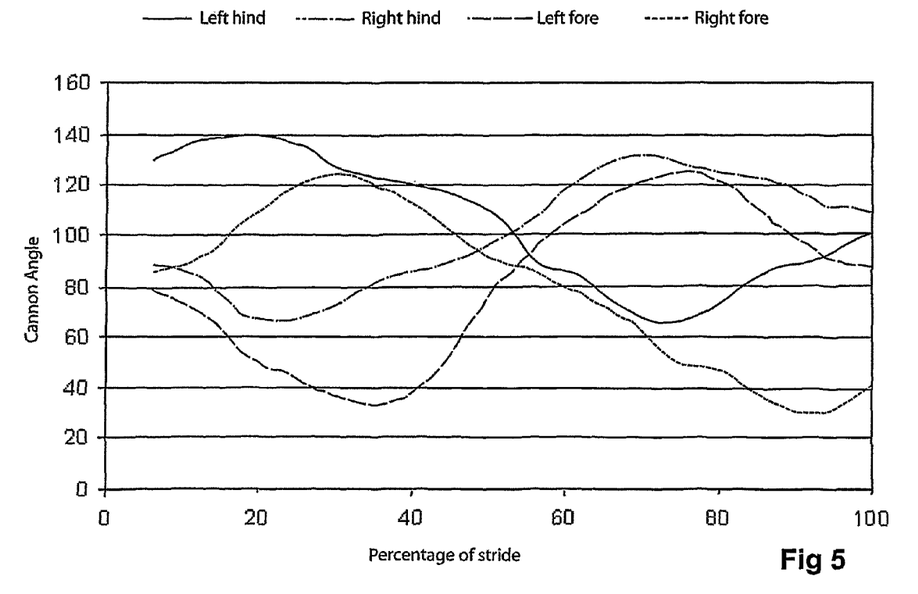
FIG. 5 shows the cannon angles taken from the published Muybridge still photos at a trot taken over 100 years ago.
Figure 6:
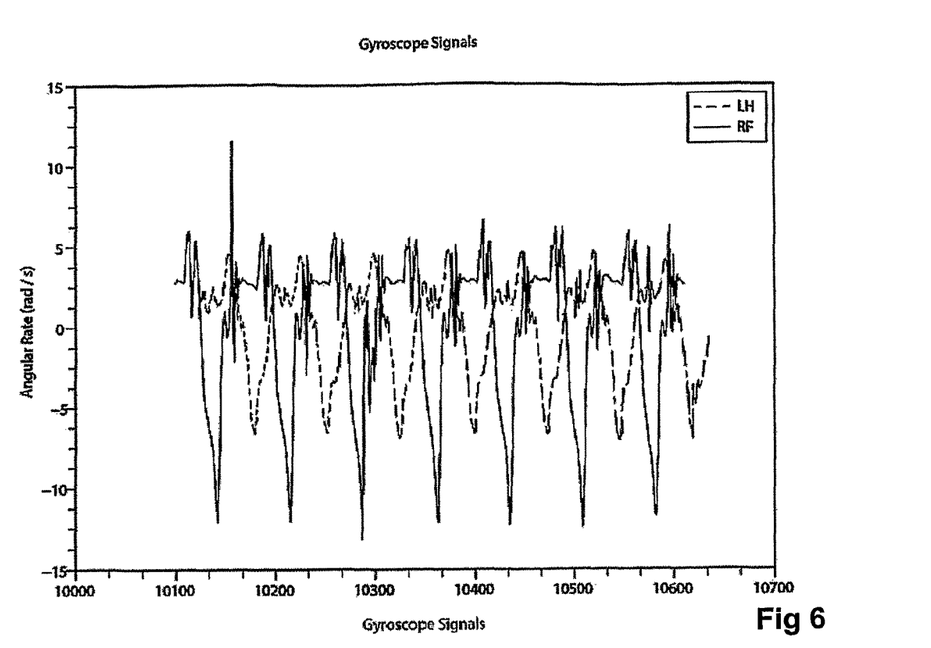
FIG. 6 shows the output from the gyroscopes with no sample delay applied.
Figure 7:
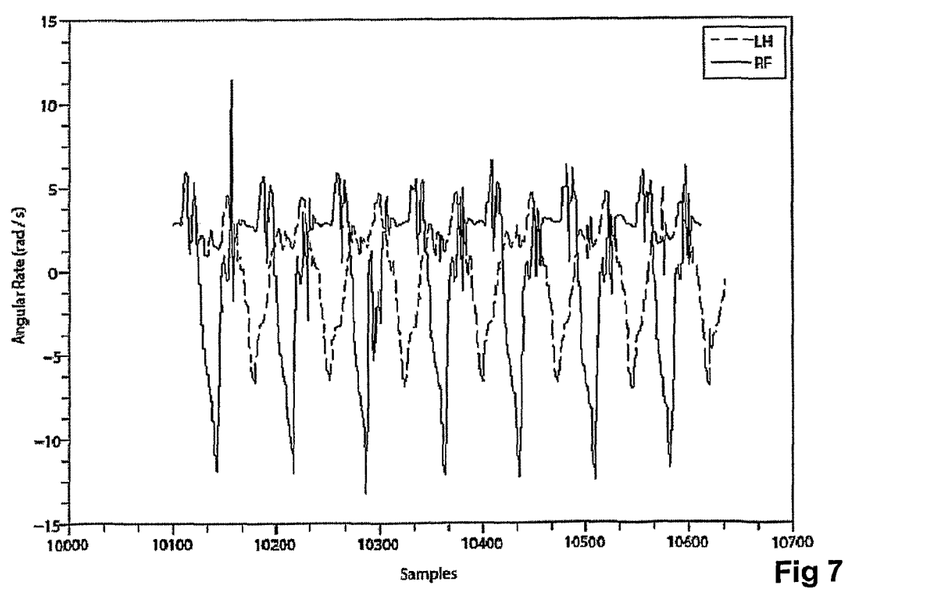
FIG. 7 shows the output from the gyroscopes with a delay of 25 samples applied.
Figure 8:
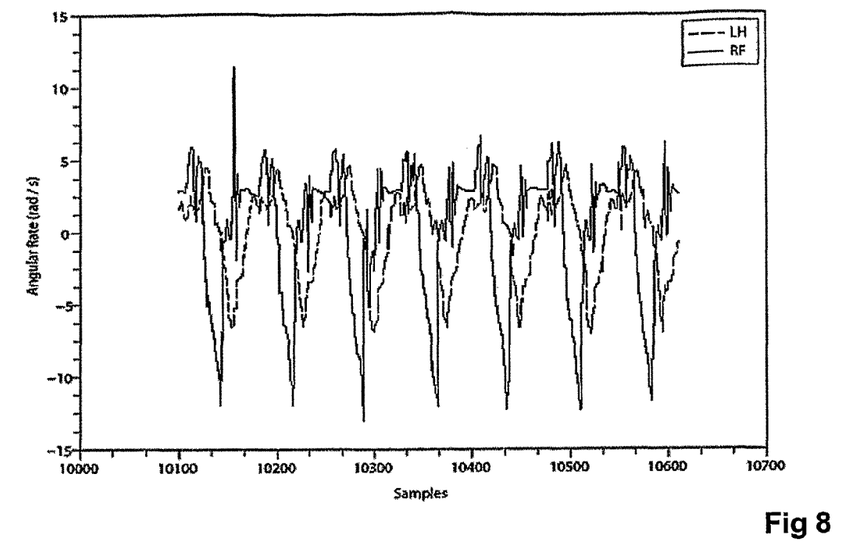
FIG. 8 shows the output from the gyroscopes with a delay of 59 samples applied.

FIG. 5 shows the cannon angles for the four legs of a horse when in trot, taken from photographs taken by Muybridge and which are well known in the art. Using the system described above, FIGS. 6 to 8 slow the gyroscope outputs from a 512 sample window taken from a recording of a horse in trot. The width of the window is important. The wider the window the more accurate will be the result, because the cross-correlation will operate over more cycles of the waveforms. However, this must be balanced against the need to maintain a steady gait over a long period of time. The minimum window width must be at least one full period of both waveforms, implying at least one and a half strides in the gait. For a slow walk at about 0.8 Hz this would require nearly two seconds. A compromise of 256 samples, or approximately 2.5 seconds, was felt to be suitable. The signals are taken from the gyroscopes that measure the axis of rotation perpendicular to the direction of forward motion of the animal and in the plane tangential to the gravity vector. This axis is approximately the hinge axis of the knee or the hock joint and therefore provides the maximum signal. FIGS. 6 to 8 show the cross-correlation between the left hind and the left fore limbs. The time shift is applied to the left hind traces, and the result is therefore the phase lag of the left fore limb with respect to the left hind limb.

Figure 9:
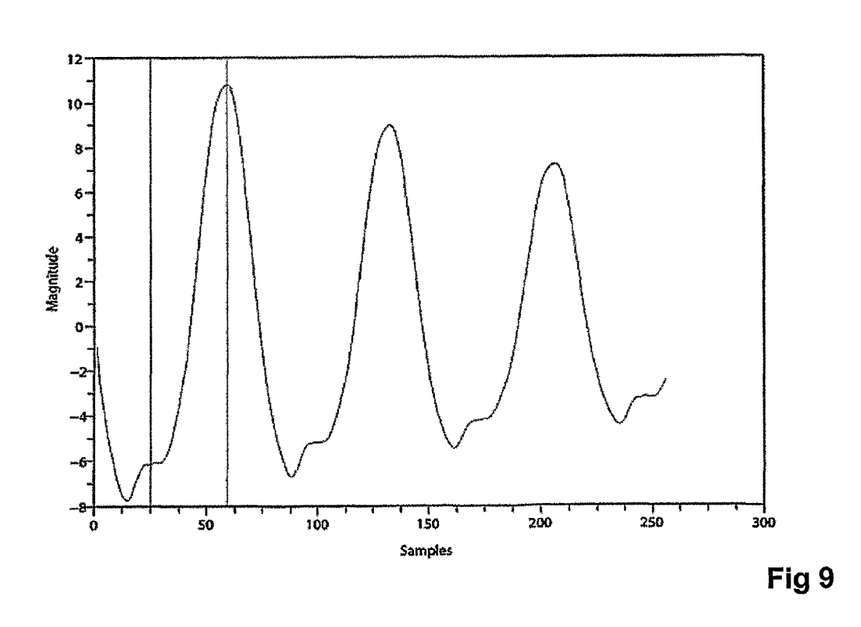
FIG. 9 shows the cross-correlation output.

The magnitude of the cross-correlation function at a 25 sample delay as shown in FIG. 7 is shown in FIG. 9 by the line x=25 marked on that figure, where the x axis corresponds to the number of samples of delay added to the left hind signal;

that line marks the point at which the delay is 25 samples and the value of the correlation function is approximately −6. The line x=59 marks the point at which the delay is 59 samples and the value of the correlation function is at its maximum of nearly 11. The magnitude of the cross-correlation function at a delay of 59 samples as shown in FIG. 8 is also shown in FIG. 9, by the line x=59. In fact this is the point at which the correlation function is a maximum and is therefore the point of closest match. The cross-correlation output for this example is shown in FIG. 9. The phase lag of the left fore limb with respect to the left hind limb is therefore 59 samples.

In order to convert the sample delay into a phase, it was necessary to identify the period of the cycle. When a function is correlated against itself, the cross-correlation function becomes the auto-correlation function. Care must be taken interpreting the output of the auto-correlation function, since a zero delay must necessarily produce the maximum value because it corresponds to the square of the function. However, the second peak occurs when the delay is equal to the period of the function. As a phase angle this corresponds to radians, but here it is convenient to quote the phase as a percentage of stride period.

The processed signals describe the temporal phase difference of the limbs relative to a reference limb and are expressed as a percentage of the reference limb stride cycle. At a walk, the median values are 33, 49 and 81%. At a trot on the hard surface, the average values are 15, 50 and 65%. At a canter on the soft surface on the left rein, the values are 25, 30 and 53%.

Figure 10A:
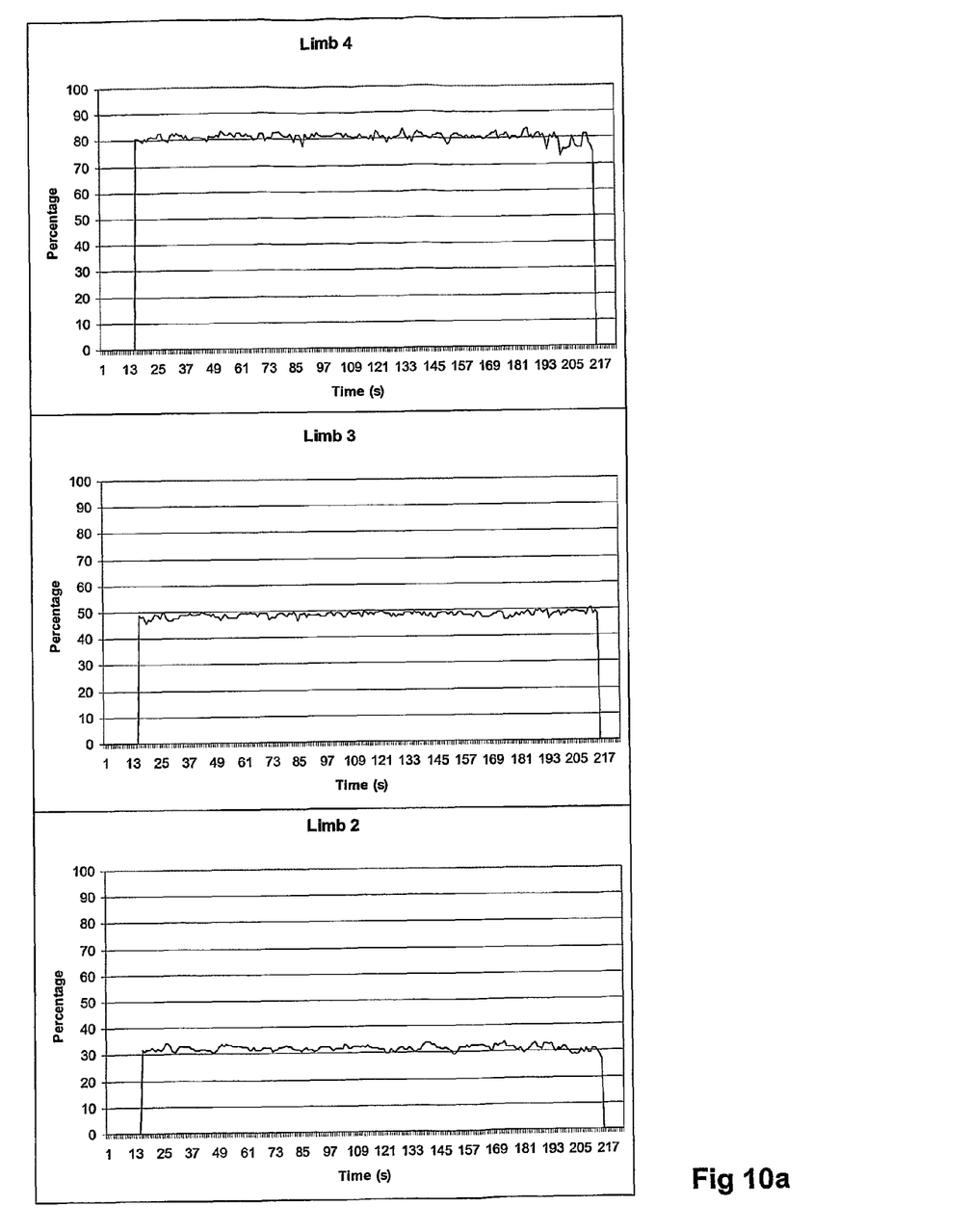
FIG. 10*a* shows processed signals from horse 1 walking in straight lines on a hard surface.
Figure 10B:
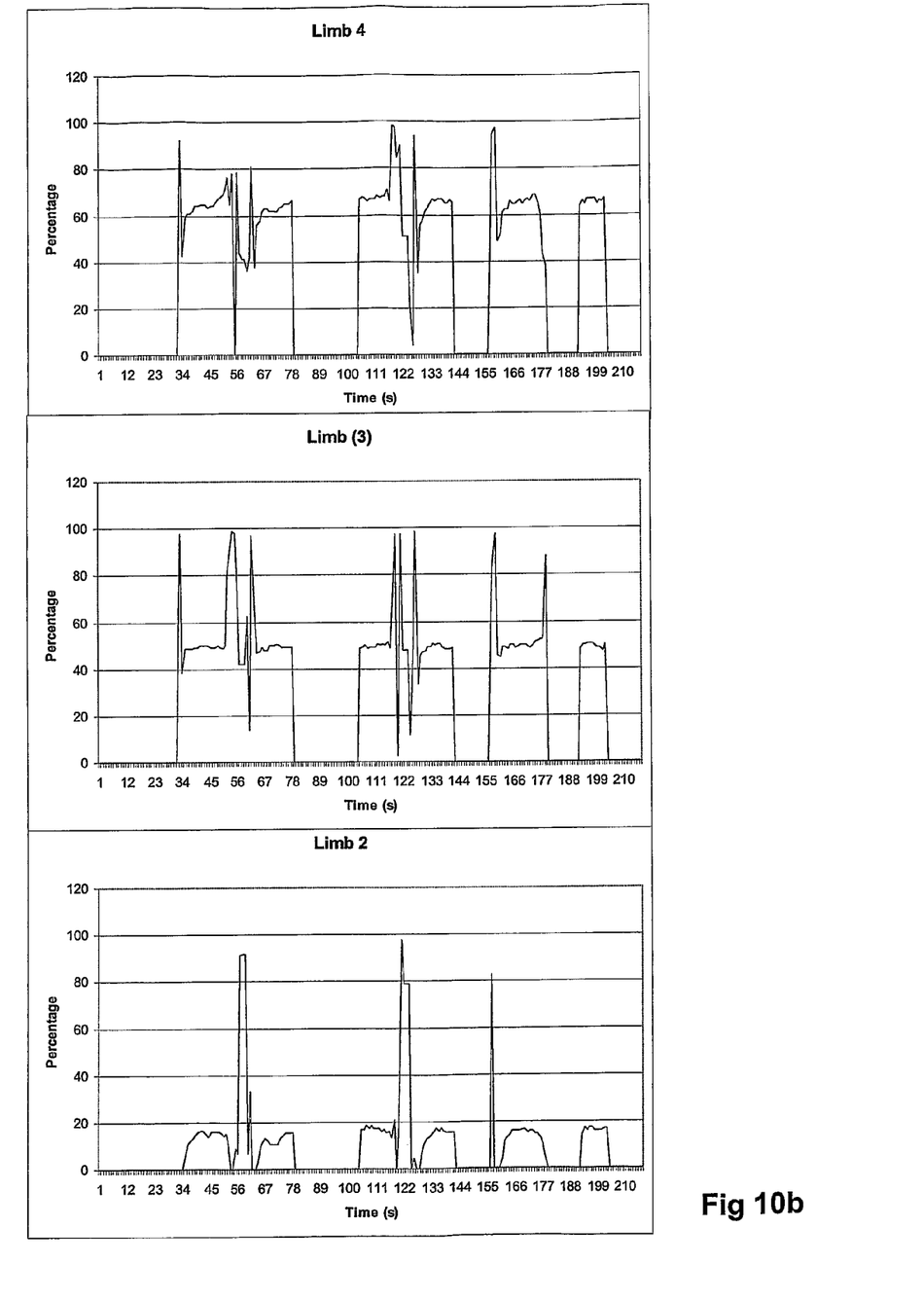
FIG. 10*b* shows processed signals from horse 1 walking in straight lines on a soft surface.
Figure 10C:
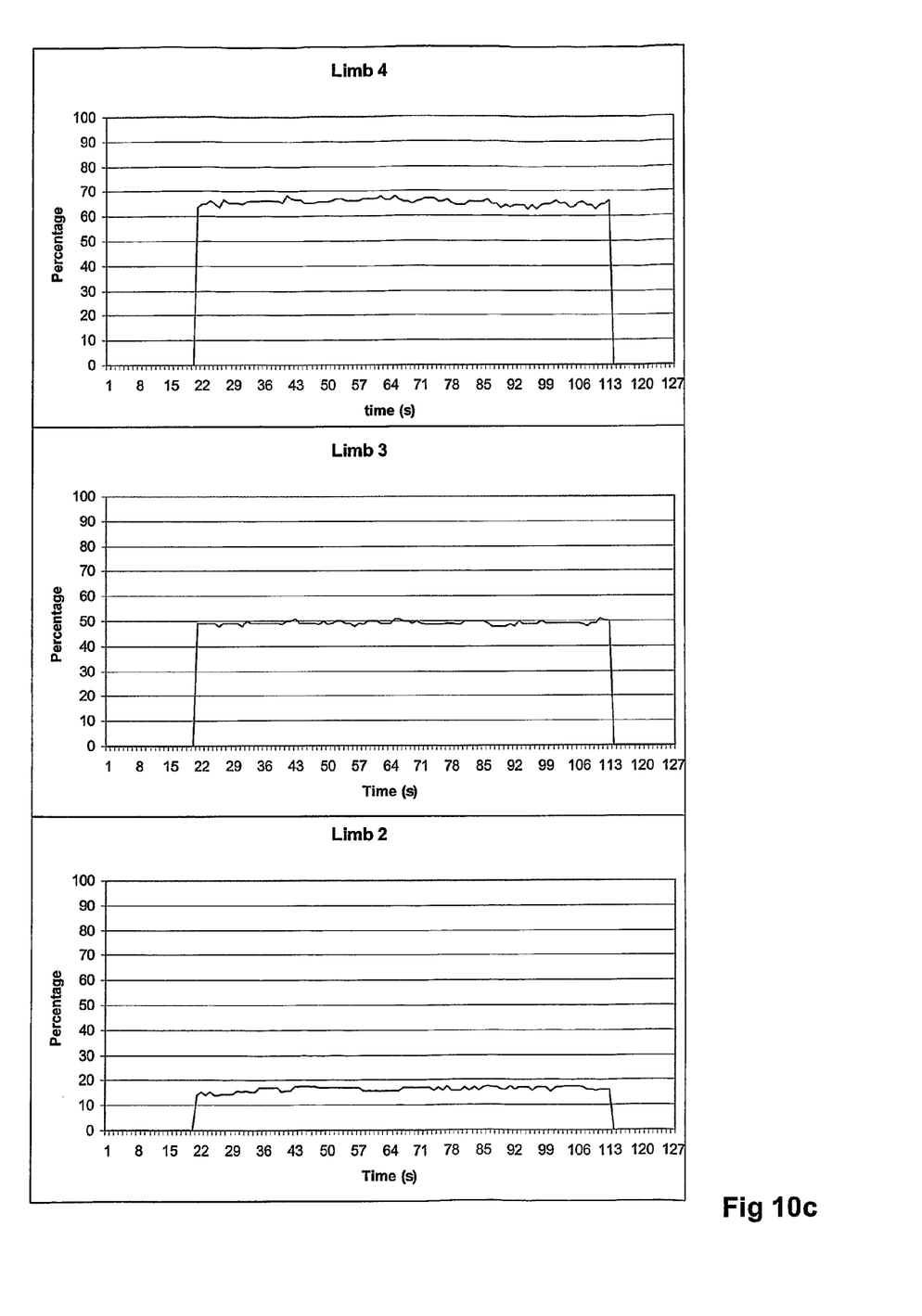
FIG. 10*c* shows trotting in straight lines on a hard surface.
Figure 10D:
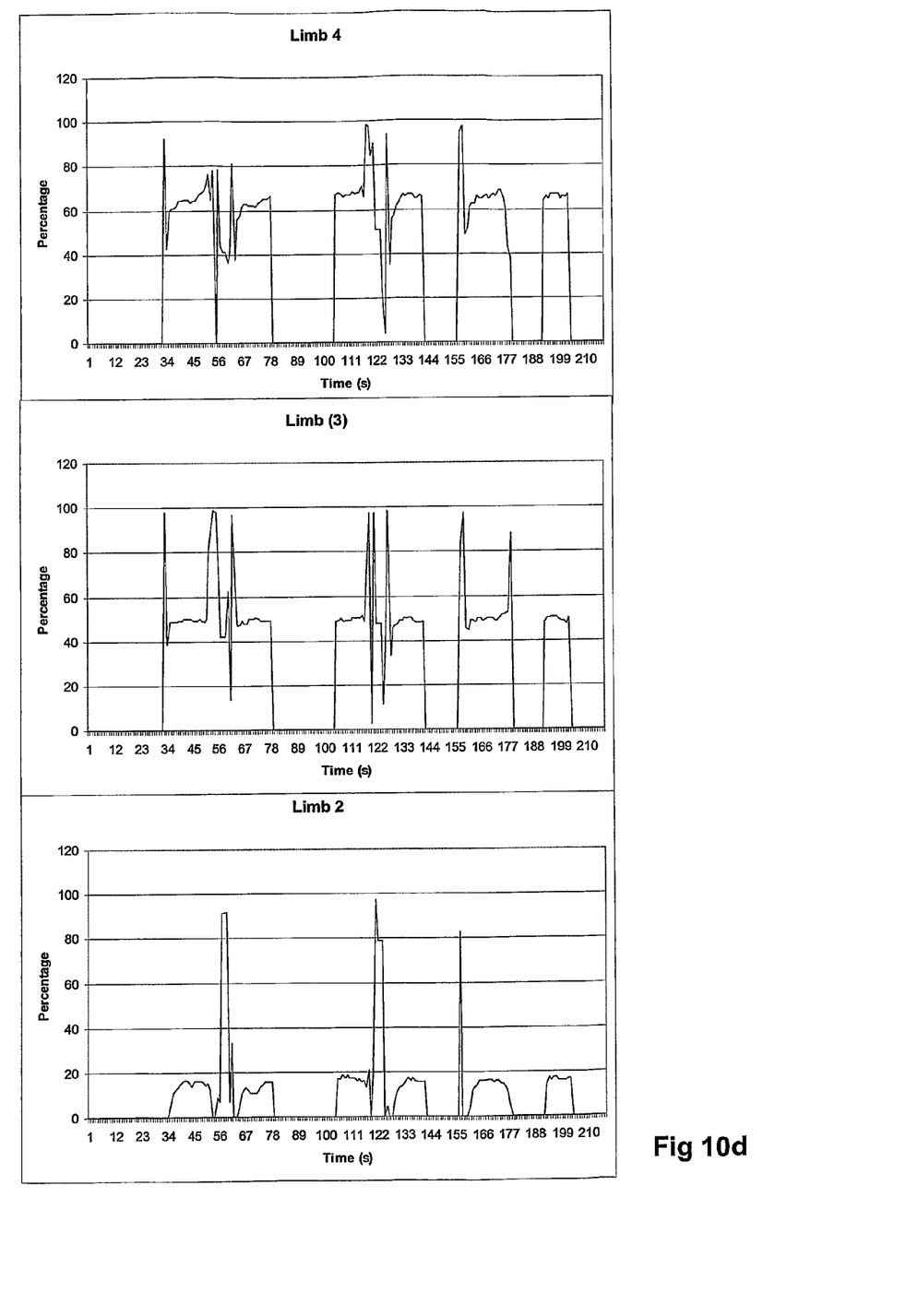
FIG. 10*d* shows trotting in straight lines on a soft surface.

As mentioned above, FIGS. 10a and 10b show processed signals from horse 1 walking in straight lines on hard and soft surfaces respectively and FIGS. 10c and 10d are for the same horse trotting in straight lines on hard and soft surfaces respectively. Each individual limb cycle is represented as the percent the temporal phase shift occurs in comparison to the reference limb (limb 1) stride cycle. The signal from b and d on the soft surface clearly shows where the horse stopped and turned between each diagonal length.

Figure 11A:
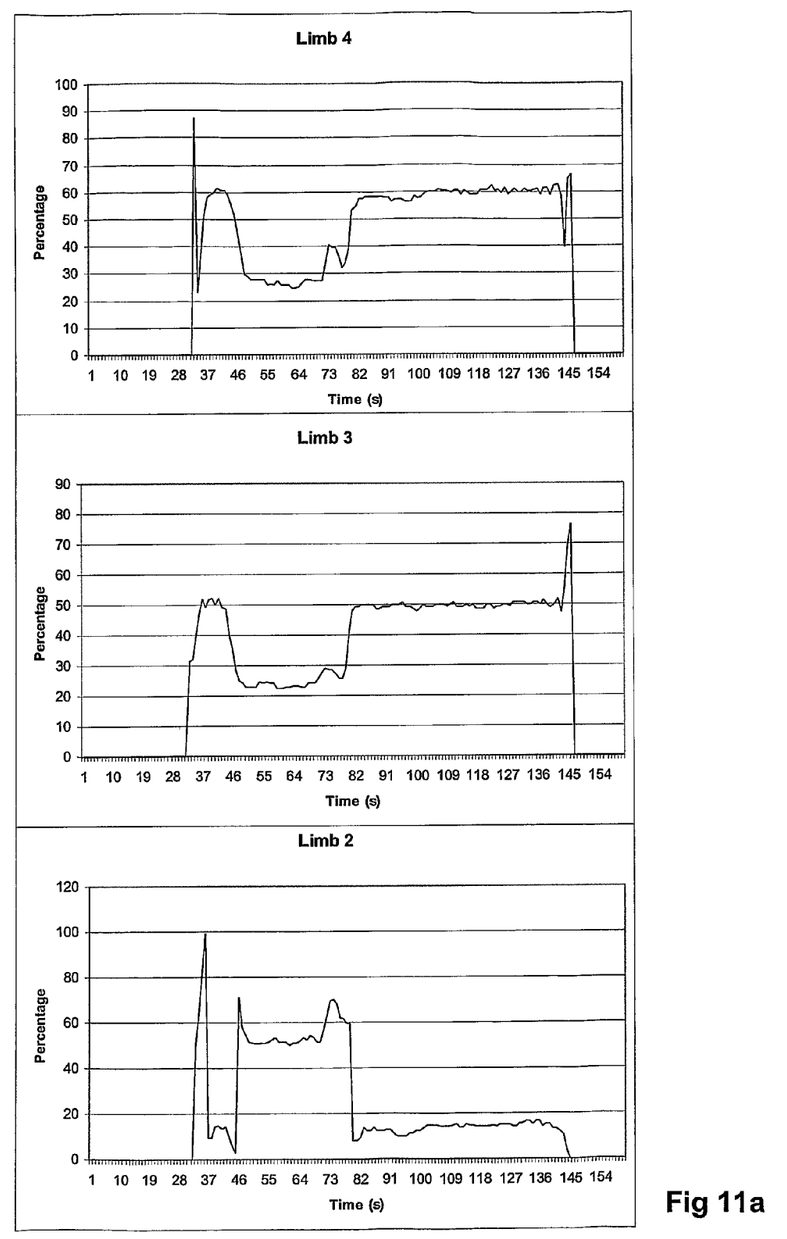
FIGS. 11a and 11b show processed signals from horse 2 showing cantering to trotting on left (a) and right (b) circles.
Figure 11B:
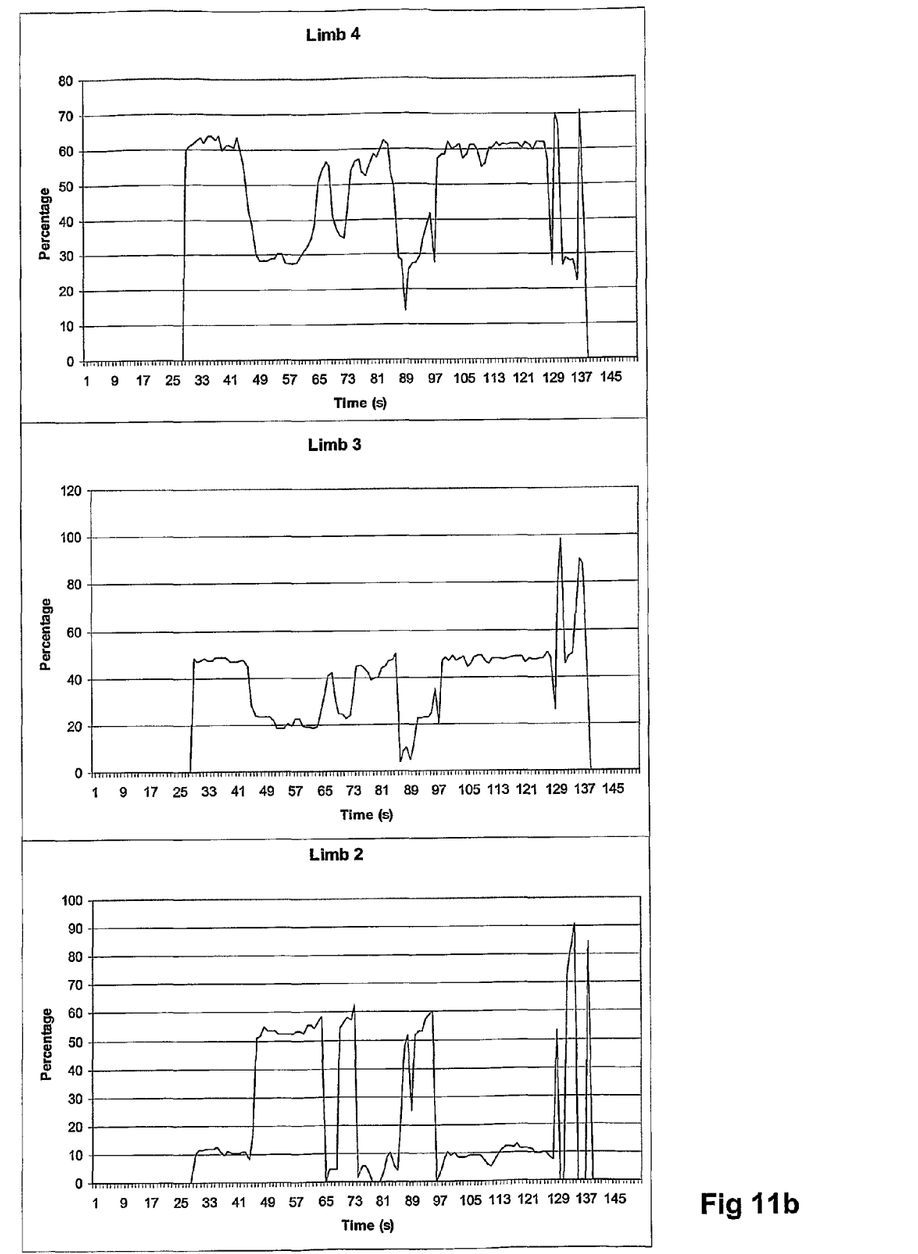

FIGS. 11a and 11b show processed signals from horse 2 when cantering to trotting in left-hand and right-hand circles respectively. The transitions between trot and canter are clearly indicated by a change in limb cycling, proportional to the reference limb (limb 1). Horse 2 started the left circle (a) in trot between 7 and 16 seconds where a transition to canter occurred. Cantering was maintained and a transition to trotting occurred at 50 seconds. The right circle (b) shows a less steady canter with a transition from trotting to cantering at 20 seconds, a broken trot-canter-trot between 39 to 60 seconds followed by a canter until 70 seconds, then trotting.

The gyroscope output about the joint axis (the z-axis) provided a reliable method of correlating signals from individual limbs on any surface in any gait, from the obtained clear cyclic signal shapes. When performing the auto-correlation function the gyroscope outputs for all limbs correlate for all gaits on a range of surfaces, making it a suitable for phase difference timing.

The results of the signal processing demonstrate the robustness of the technique. The correlation function is a mathematical method for determining the phase relationship between two signals. The method does not require any subjective input, such as an operator determining when a particular event has happened. The integration of the product of the correlation waveforms improves the signal to noise ratio and thereby reduces the noise present on individual strides, particularly as the width of the window is increased.

The technique is independent of amplitude and offset mismatch and is therefore extremely tolerant of unit misalignment and temperature drift. The measurement method is unconstrained and capable of recording long periods of movement resulting in the possibility of profiling limb cycle temporal phase difference relationships.

The measurement method is independent of and can be used for, all gait types on any surface.

Explanation for a Human

In the case of a human the temporal phasing between the left and right limb should be 50 percent if the gait is symmetric. This can be determined by comparing the sensor data from the same portion of each limb e.g. the calf or thigh.

The phasing between the calf and thigh will be specific to the way an individual moves. However, again for symmetry the difference between the calf and thigh temporal phasing should be the same for both limbs, with a symmetric gait.

Therefore, asymmetries can be determined by comparing the phasing of one or more units on both limbs, e.g.

|  | Symmetric Gait | Asymmetric Gait |
|---|---|---|
| Left Calf | Reference | Reference |
| Left Thigh | 20% | 18% |
| Right Calf | 50% | 48% |
| Right Thigh | 70% | 70% |
| Right Calf − Left Calf − 50% | 0% | −4% |
| (Right Thigh − Right Calf) − (Left Thigh − Left Calf) | 0% | 4% |

In the case of the asymmetric gait the right calf temporal movement is earlier by 2% of the stride duration and the right thigh moves later over the right calf, when compared to the left thigh, left calf movement. This would result in a different joint angle with time between the left and right leg.

Explanation for a Horse

For a horse in a symmetric gait (walk or trot) the temporal limb phasing between the two hind limbs and the two for limbs should be 50%. Also in the trot the temporal phasing between a hind limb and the corresponding diagonal fore limb should be the same. Therefore, by monitoring trot as a symmetric gait any asymmetries in the temporal movement can be determined.

By way of example if the temporal limb phasing is determined by placing a sensor unit on the same part of each limb e.g. the metacarpal/carpal bone then any temporal asymmetry in the gait can be determined.

|  | Symmetric Gait | Asymmetric Gait |
|---|---|---|
| Left Hind | Reference | Reference |
| Left Fore | 10% | 12% |
| Right Hind | 50% | 48% |
| Right Fore | 60% | 58% |
| (Right Hind − Left Hind) − 50% | 0% | −2% |
| (Right fore − Right Hind) − (Left Fore − Left Hind) | 0% | −2% |

In this example the right hind temporal movement is 2% earlier than it should be and the right fore movement is also 2% earlier.

Comparison with Other Temporal Phasing Methods

The temporal limb phasing obtained using the cross correlation method differs from other published data where events on the different limbs have been compared. This can be explained by referring to FIG. 4. The two sine waves can be taken as the cyclic motion on the fore and hind limbs. The small disturbances can be taken as the hoof contact point.

Using the cross correlation method the phase between the two signals would be 50 samples, but if the disturbances were aligned it would be 60 samples.

Referring to motion data for a horse at a trot, obtained by the method of Muybridge, which has been translated into the movement of the cannon on each limb over the stride duration by the method of this invention as shown in FIG. 5, it is clear that the rear limbs move in advance of the fore limbs. The rear limb leads to fore limb by approximately 15%, which is in line with the findings in this paper. The event of foot down therefore occurs at a different point on the cannon movement cycle for the rear and front limbs at trot.

The invention claimed is:

1. A method of monitoring or assessing the motion of the limbs of a human or animal body when performing repetitive cyclic activity, comprising the steps of:
   securing a respective sensor measurement unit to each of the limbs to be monitored, each sensor measurement unit being associated with a receiver for data generated thereby;
   synchronising the operation of the sensor measurement units;
   assembling and analysing the data from the sensor measurement units to determine the relative phase of the limb movements in the course of the performance of the repetitive cyclic activity using cross-correlation techniques.

2. A method as claimed in claim 1, wherein the assembled data is indicative of at least one of limb rotation and joint rotation.

3. A method as claimed in claim 1, wherein the assembled data is indicative of at least limb spatial position as the limb moves in the course of the cyclic activity.

4. A method as claimed in claim 1, wherein the data from each sensor measurement unit is stored locally in the receiver for subsequent up-loading to a computer wherein the data is analysed for an assessment of the phasing of the limbs during the cyclic activity.

5. A method as claimed in claim 1, wherein the data from each sensor measurement unit is transmitted in real time to a data receptor and then is loaded in to a computer wherein the data is analysed for an assessment of the phases of the limb movements.

6. A method as claimed in claim 1, wherein each sensor measurement unit comprises at least one gyroscope and at least two accelerometers, arranged to sense movement with two degrees of freedom.

7. A method as claimed in claim 6, wherein each sensor measurement unit includes a tri-axial accelerometer.

8. A method as claimed in claim 7, wherein each sensor measurement unit includes three single-axis gyroscopes with their sensing axes arranged mutually orthogonally.

9. A method as claimed in claim 1 and specifically adapted for use in assessing the gait of a horse, wherein each sensor measurement unit is secured to the cannon of a horse's leg.

10. A method as claimed in claim 9, wherein sensor measurement unit defines a z-axis gyroscope and the outputs of the z-axes are used to correlate rotational limb function.

11. A method as claimed in claim 1 and specifically adapted for use in assessing the gait of a horse, wherein the sensor measurement units are arranged to sense joint angle and the sensed angles are correlated to assess the relative phases of the limbs when performing cyclic activity.

12. A method as claimed in claim 11, wherein a separate phase assessment is made for at least two different gaits of the horse and the separate phase assessments are compared to obtain relative phasing data of the limb movements.

13. A method as claimed in claim 11, wherein the sensor measurement units are secured to the horse's limbs to determine one of fetlock joint rotation or fore knee joints (on the fore legs) and hind hock joints (on the hind legs).

14. A method as claimed in claim 1, wherein each sensor measurement unit comprises a MEMS (microelectromechanical systems) device.

15. A method as claimed in claim 1 and adapted for use in assessing asymmetries between the left and right leg of a human.

16. A method as claimed in claim 1, wherein a separate phase assessment is made for at least one location on each limb and stride duration and the relative phasing is determined.

17. A method as claimed in claim 1, wherein a separate phase assessment is made for at least two locations on each limb to determine any asymmetries in temporal movement between comparable locations.

18. A method as claimed in claim 2, wherein the assembled data is further indicative of at least limb spatial position as the limb moves in the course of the cyclic activity.

* * * * *